United States Patent
Grosskopf et al.

(10) Patent No.: US 7,894,873 B2
(45) Date of Patent: Feb. 22, 2011

(54) METHOD FOR DETERMINING THE RECTUM DISTANCE IN THE COLON

(75) Inventors: Stefan Grosskopf, Nürnberg (DE); Lutz Gündel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 878 days.

(21) Appl. No.: 11/399,500

(22) Filed: Apr. 7, 2006

(65) Prior Publication Data

US 2006/0251308 A1 Nov. 9, 2006

(30) Foreign Application Priority Data

Apr. 8, 2005 (DE) ........................ 10 2005 016 258

(51) Int. Cl.
*A61B 5/05* (2006.01)
(52) U.S. Cl. ...................................... 600/407; 382/128
(58) Field of Classification Search ................. 600/101, 600/425, 427; 382/128, 131, 173, 276, 282, 382/284, 294
See application file for complete search history.

(56) References Cited

U.S. PATENT DOCUMENTS 7,224,827 B2 * 5/2007 Acar et al. .................. 382/131

2004/0136584 A1 7/2004 Acar et al.

FOREIGN PATENT DOCUMENTS

EP 1 057 161 B1 5/2002

OTHER PUBLICATIONS

Studholme, C. Simultaneous Population Based Image Alignment for Template Free Spatial Normalisation of Brain Anatomy. Lecture Notes in Computer Science: Biomedical Image Registration. p. 81-90. Nov. 4, 2003.*
Wan, Ming et al. "Automatic Centerline Extraction for Virtual Colonoscopy." IEEE Transactions on Medical Imaging, vol. 21, No. 12, Dec. 2002, pp. 1450-1460.
Acar et al. "Medial Axis Registration of Supine and Prone CT Colonography Data." Proceedings of the $23^{rd}$ Annual EMBS International Conference, Oct. 25-28, 2001, pp. 2433-2436.
Timo Mäkelä et al.: "A Review of Cardiac Image Registration Methods", IEEE Transactions on Medical Imaging, vol. 21, No. 9, Sep. 2002, pp. 1011-1021.

* cited by examiner

*Primary Examiner*—Brian Casler
*Assistant Examiner*—Parikha S Mehta
(74) *Attorney, Agent, or Firm*—Harness, Dickey & Pierce

(57) ABSTRACT

A method is disclosed for automatically determining the rectum distance in a patient's colon, the path in the colon between a selected site, preferably a lesion, and the rectum being determined by processing 3D image data records. At least two 3 image data records are recorded with the patient being differently positioned. Further, the path between the rectum and selected site is determined from the common perusal of the at least two 3D image data records.

20 Claims, 6 Drawing Sheets

METHOD FOR DETERMINING THE RECTUM DISTANCE IN THE COLON

The present application hereby claims priority under 35 U.S.C. §119 on German patent application number DE 10 2005 016 258.4 filed Apr. 8, 2005, the entire contents of which is hereby incorporated herein by reference.

FIELD

The invention generally relates to a method for automatically determining the rectum distance in a patient's colon, the path in the colon between a selected site, preferably a lesion, and the rectum being determined by processing 3D image data records.

BACKGROUND

A method for automatically determining the rectum distance in the colon is known from the European patent specification EP 1 057 161 B1. It is described there how it is possible by automatically determining a path in 3D image data records of colon displays, to determine the path between a lesion in the colon and the rectum. Reference is also made by way of example to the use of the Dijkstra method for finding the shortest path on a graph.

The problem with such methods in which the path calculation is carried out automatically from a 3D display of a patient's colon resides in the fact that, depending on the position in which the 3D display is recorded, parts of the colon cannot be completely continuous. Consequently, the automatic method cannot lead to the goal in the case of such displays, but must be stopped prematurely.

SUMMARY

It is an object of at least one embodiment of the invention to provide a method that enables the rectum distance in a patient's colon to be determined automatically even when positionally defined blockages are present in the colon picture.

The inventors have recognized that the problem of a premature stoppage during automatic calculation of the rectum distance in the colon from a selected site can be circumvented by not only using a single 3D display of the patient in a single position, but taking at least two or more pictures of the patient in different positions. As a result, sites in the colon whose passage is blocked at a specific position can be opened by repositioning the patient. By common perusal of the various images of different positions of the patient, it is then possible to bridge such position-dependent blockages during automatic calculation of the rectum distance, and to determine the rectum distance automatically with a high probability of success.

The inventors propose, in accordance with at least one embodiment, to improve the method known per se for automatically determining the rectum distance in a patient's colon, in the case of which the path in the colon between a selected site, preferably a lesion, and the rectum is determined by processing 3D image data records. In at least one embodiment, the improved method includes recording at least two 3D image data records with the patient being differently positioned. Further, the path between the rectum and selected site is determined from the common perusal of the at least two 3D image data records.

There are diverse possibilities for executing the common perusal of the different 3D image data records.

A first example possibility resides in combining the available 3D displays of the patient in different positions with one another by way of a morphing method or by way of a registration such that here, as well, possible blockages in the colon path are opened, thus enabling automatic path calculation free from stoppage.

It is also possible alternatively or in addition to superpose the 3D image data records themselves, for example by way of an OR operation of the air-filled voxels of the image data records such that wherever the air-filled region of the colon is found in one of the displays a path that can actually be found is indicated in the superposed display. Blockages that are present in a display are thereby compensated in the superposed variant such that it is possible overall to carry out an automatic path calculation without premature stoppage owing to a blockage.

A further variant of at least one embodiment of the invention provides that an automatic path calculation is carried out for each of the at least two 3D image data records, and path calculations that stop before the rectum is reached remain out of account.

Moreover, it is possible that an automatic path calculation is carried out for each of the at least two 3D image data records, and in each case premature path stoppages owing to blockages are reciprocally replaced by paths of the respective other 3D image data record, the path calculation in the image data record with prematurely stopped path being resumed in this image data record after bridging. Thus, use is made here of a common perusal of the 3D image data records in which a path calculation takes place in each individual 3D image data record. As soon as a path stoppage is detected in one of the 3D image data records, the path through this inherently sealed part of the colon is replaced by a path that has been opened up by a different positioning until a free part of the colon has been reached again. Thus, the blockage respectively present is suppressed in the end by the redundancy of the pictures.

It is likewise possible to carry out automatic path calculation for each of the at least two 3D image data records, and to form the total path from the sum of the paths determined. Reference is made here to the fact that this formation of the sum does not constitute an addition of the path lengths, but that in this formation of the sum the actual geometrical paths are to be combined with reference to their position, and the total path is then calculated therefrom.

A further possibility can reside in that, for each of the at least two 3D image data records, an automatic path calculation is carried out in relation to at least one salient point in the colon, the path lengths between the salient points are determined, to the extent that this can be carried out without premature stoppage, and the total path between the predetermined site and the rectum is determined from all subpaths thus present. This variant utilizes the fact that each colon has specific characteristic features that can be determined automatically.

For example, in this case an appendix that is present is involved, or the right or left curve or the ileum. If, now, the different path lengths between the salient points and the selected site, determined in each case for different positions, are entered in a table, the entire stretch between the selected site or a lesion and the rectum can be put together by forming the mean value of all the subpaths actually found. It is not absolutely necessary in principle to form a mean value here, it is also possible to determine the most likely path by means of other mathematical methods, it being possible to take no account of outliers with reference to the length determined for a subpath. Examples are meridian values, arithmetic means or similar methods.

A further inventive variant of an embodiment of the method for automatically determining the rectum distance in a patient's colon, which can, if appropriate, also be carried out using a single picture, provides that in the case of at least one 3D image data record an automatic path calculation is carried out in relation to at least one salient point whose mean statistical distance from the rectum is constant in a fashion largely independent of patient, or is known as a function of other patient parameters (for example, size, weight or sex), and the path length to the rectum is determined from the sum of the calculated path and the distance which is known independently of patient.

In this embodiment of the method, account is taken of the fact that the path length from specific salient points in the colon to the rectum can be predicted with great reliability for a patient. It is accordingly necessary only to determine the path between such a salient point and the selected site or the lesion in the colon, in order to be able to calculate the actual path length from the selected site to the rectum. It is also possible here that the salient site need not necessarily lie on the path between the selected site and the rectum, but that it is also possible for the salient point to be located outside this route, that is to say a path is thus calculated which leads away from the rectum and deeper into the colon region, it subsequently being necessary to subtract that path found from the statistically known distance from the salient point to the rectum in order to determine the actual distance from the selected site to the rectum.

The inventors also propose in accordance with a further variant embodiment of the invention that a typical colon volume data record is produced by registering a multiplicity of colon pictures of various standard persons, and is registered with at least one picture of the currently examined patient, and an automatic path calculation relating to the rectum is determined with the aid of the image data record resulting therefrom.

The method of registering various volume image data records is known, for example, from cardio imaging. Reference is made in this regard to the document by Timo Mäkele et al., A Review of Cardiac Image Registration Methods, IEEE Transactions on Medical Imaging, Vol. 21, No. 9, September 2002, 1011-1021, the entire contents of which are incorporated herein by reference, with citations of literature that lead further. This method is explicitly explained again in the description of the figures that follows.

Also possible, moreover, is a combination in the case of which a typical colon volume data record is produced by registering a multiplicity of colon pictures of various standard persons, and is registered at least partially with at least one picture of the currently examined patient, and an automatic path calculation relating to at least one salient point is carried out with the aid of the image data record resulting therefrom, and from the sum of this distance and the known distance of this salient point the distance to the rectum is determined from the typical colon volume data record (colon atlas) known by registration of a multiplicity of colon pictures of various standard persons.

In the abovenamed the method, it is possible in a way according to an embodiment of the invention to begin the path calculation either exclusively at the predetermined site in the colon, or to do so exclusively at the rectum. However, there is also the possibility of carrying out the path calculation from both ends, a greater part of the possible path to be calculated being present in this variant in the event of a blockage that is present and a premature path stoppage.

The method is preferably carried out with reference to the path calculation by using the Dijkstra method.

BRIEF DESCRIPTION OF THE DRAWINGS

Additional features and advantages of the invention emerge from the following description of example embodiments with reference to the drawings, only the features required to understand the invention being illustrated.

The aim is to explain the invention in more detail with the aid of the embodiments and drawings, the following reference symbols being used: A: vermiform appendix; $C_x$: colon; L: lesion; P, $P_x$: salient points; R: rectum; $T_x$: path; $V_x$: blockage.

Figure 1:
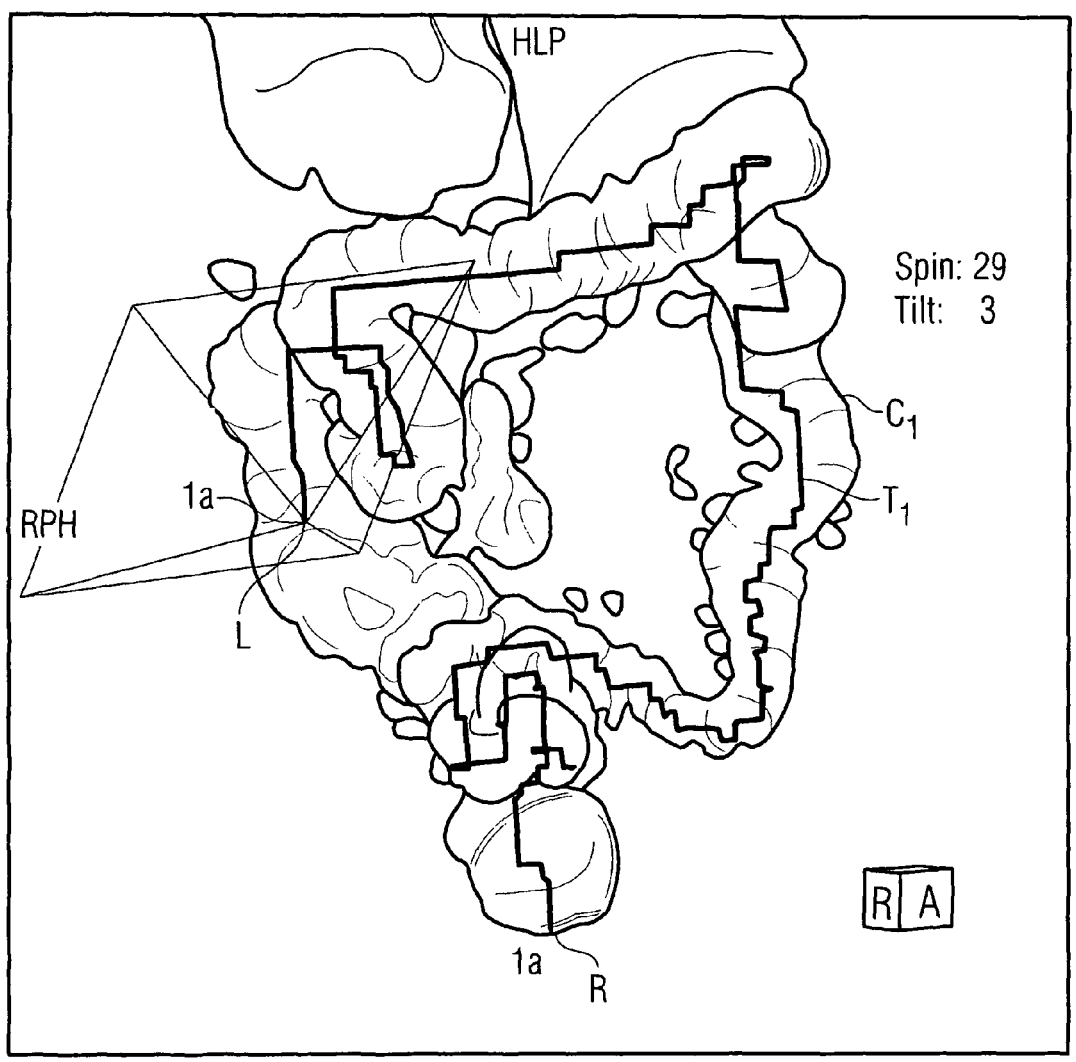
Figure 2:
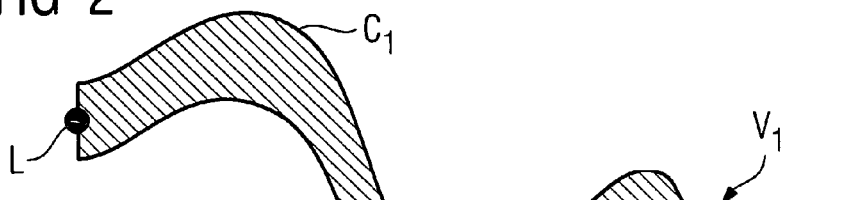
Figure 3:
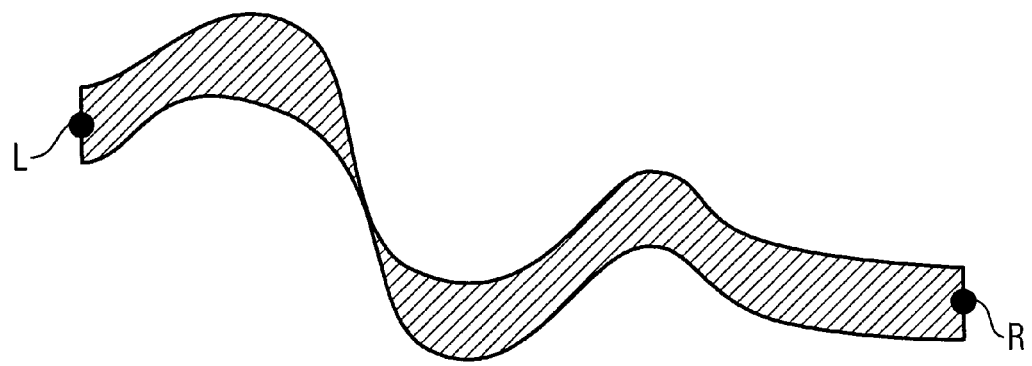
Figure 10:
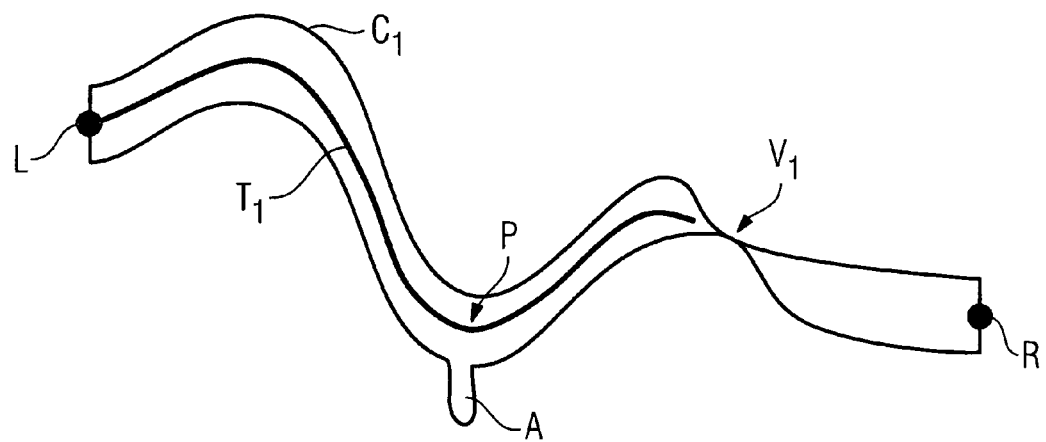
Figure 11:
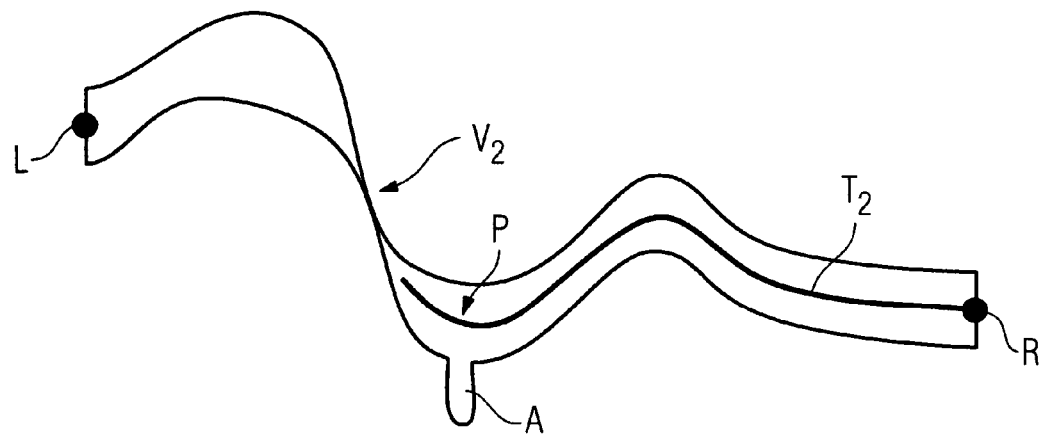
Figure 12:
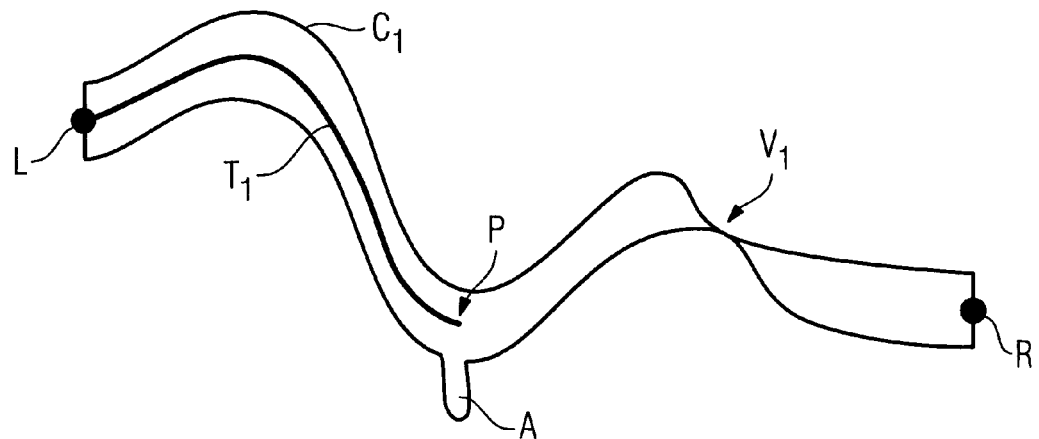
Figure 13:
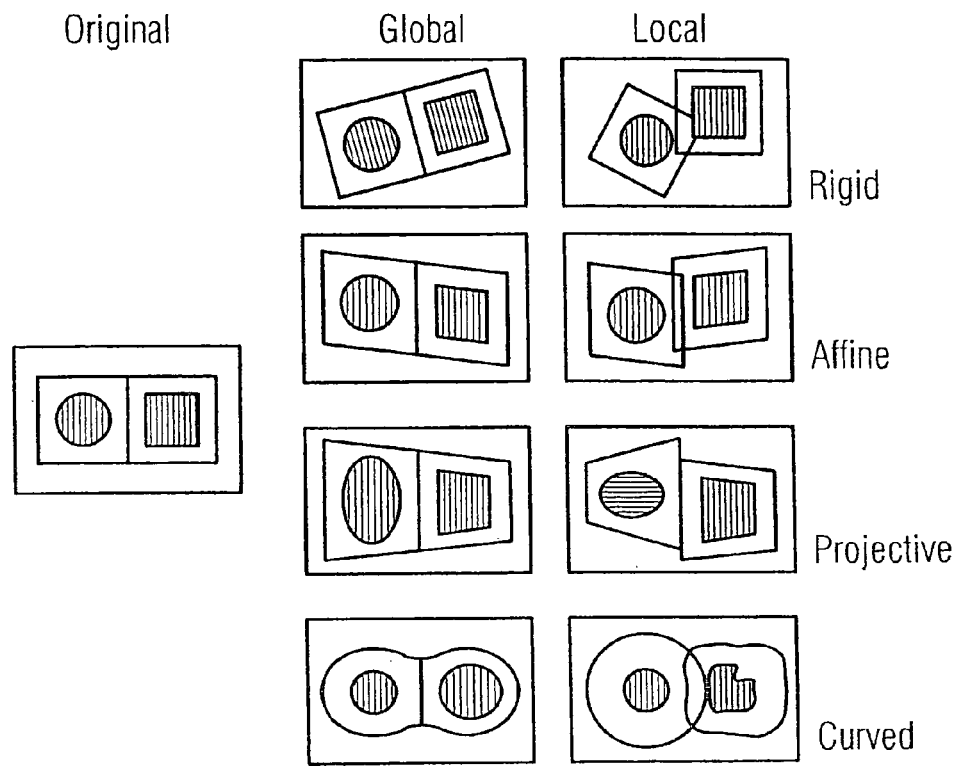
Figure 14:
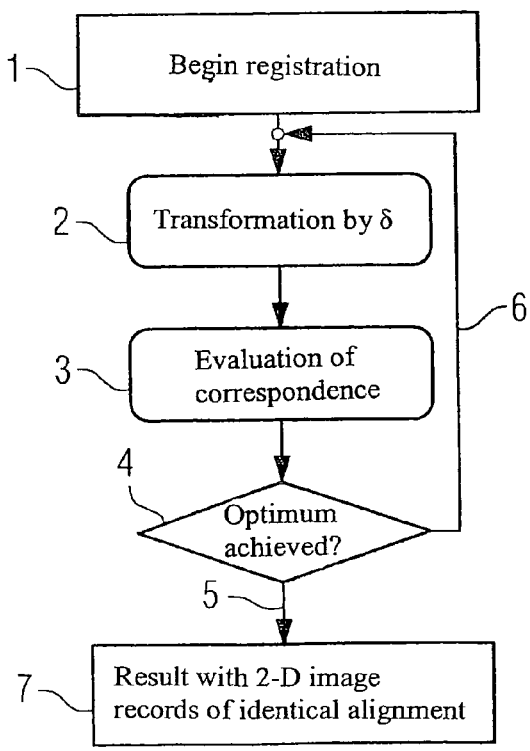
Figure 15:
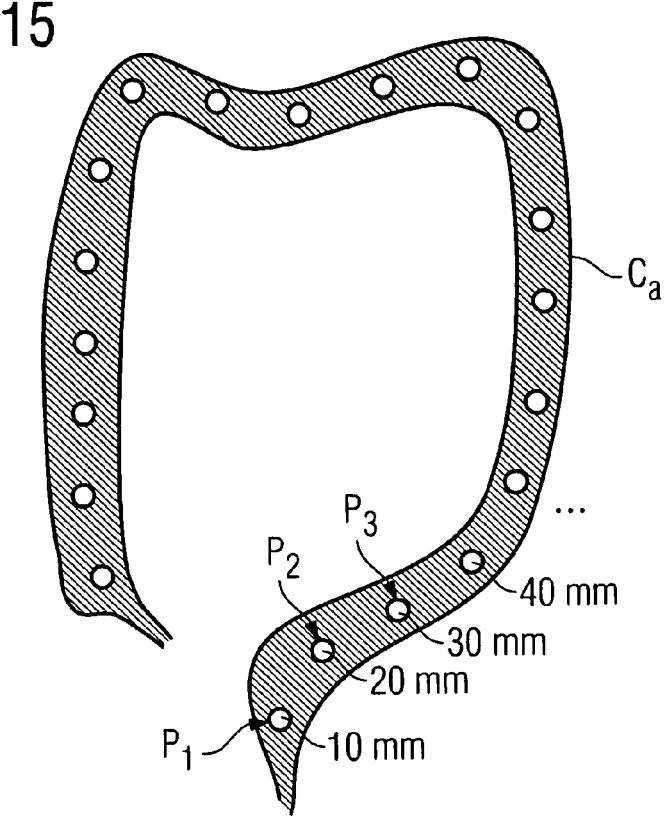

In detail:

FIG. 1: shows an example illustration of a colon picture with an illustration of the calculated path in the colon;

FIGS. 2-5: show simplified illustrations of a superposition of two colon courses from two different patient positions, with subsequent calculation of the path;

FIGS. 6-9: show simplified illustrations of the path calculation from two colon illustrations with a different position, and subsequent determination of the total path by forming the sum of the individual automatically determined paths;

FIGS. 10-11: show simplified illustrations of the method for determining distance with the aid of a secant intermediate point in the colon, here the vermiform appendix;

FIG. 12: shows a schematic of a variant of the path calculation up to the next salient point, the total distance to the rectum subsequently being determined by adding this actually measured path and the statistically known salient point in the colon to the rectum;

FIG. 13: shows schematic examples of a registration;

FIG. 14: shows a registration cycle;

FIG. 15: shows a colon atlas produced by registration; and

Figure 16:
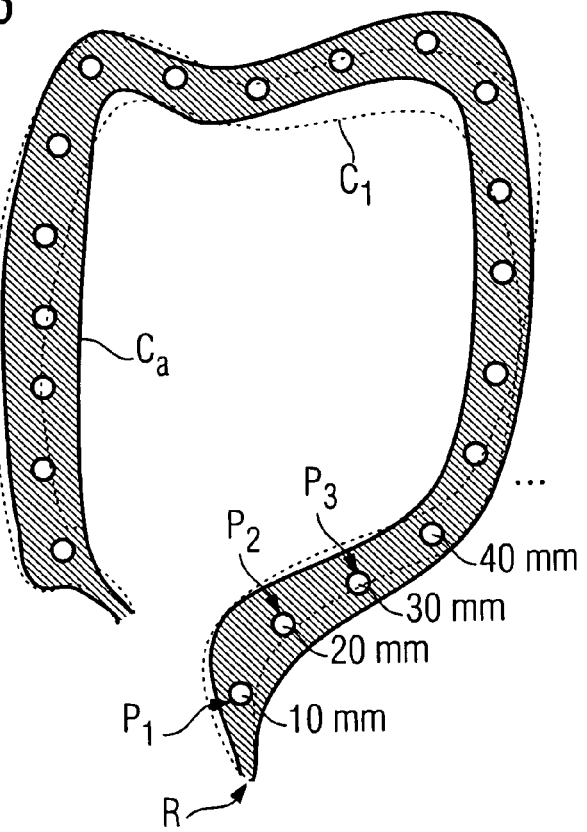

FIG. 16: shows superposition of a colon in accordance with the colon atlas and a current colon picture.

DETAILED DESCRIPTION OF THE EXAMPLE EMBODIMENTS

A three-dimensional CT picture of an air-filled colon $C_1$ is illustrated in FIG. 1, the path $T_1$ in the colon $C_1$ from a lesion L which has been found to the rectum R, which was calculated by means of an automatic method, already being entered. Such a computer-aided determination of the path through the colon can be carried out as follows, for example:

3-dimensional medical image data are acquired in many medical situations for the diagnosis of the anatomy and pathology of the colon of a patient, this being done with the aid of scanners, for example X-ray computer tomographs, NMR tomographs or ultrasonic scanners. The virtual colonoscopy supports the diagnostician in the evaluation of the image data obtained. In this case, an image processor reconstructs 3-dimensional views of the surface of the air-filled interior of the colon, views which are along the lines of views provided by a physical endoscope.

So that the user of virtual colonoscopy can find specific sites in the colon in subsequent interventional colonoscopy, the respective rectum distance of this salient site is determined. This distance datum indicates to the diagnostician how far the endoscope has to be advanced in the colon during interventional colonoscopy in order to reach the region of the site being considered.

From a geometric point of view, the rectum distance is the shortest distance to the ambient air from a specific site along the course of the colon.

The first step in image processing is to mark those voxels (pixels) in the image data that include air and/or ambient air. Subsequently, the distance measurement is used to determine, along the course of the colon, the shortest distance between the selected starting point and the nearest voxel marked as ambient air.

In the case of a modality-specific method that relates to the X-ray absorption values determined in the case of an existing computer tomographic 3D image data record, the density value of air lies below a specific threshold value such that the identification of all the air voxels is firstly carried out thereby.

During marking of the ambient air, a method examines the 2-dimensional neighborhood relationships of the air voxels in slices perpendicular to the longitudinal axis of the patient. In each slice, the starting point of the analysis is points of which it can reliably be assumed that they lie in the ambient air, for example the four corner points of the respective slice. All the air voxels of the slice that have a direct neighbor that it was possible to identify as ambient air are marked in a number of iterations. Since the colon in these slices is connected to the ambient air only at the rectum, air voxels in the colon are not marked here.

With the aid of the Dijkstra method proceeding from the starting point, the distance measurement seeks rectilinear route segments of defined length in essentially all six directions of the principal Cartesian axes (X+, X−, Y+, Y−, Z+, Z−) which run entirely along air voxels. Since the starting point is selected in the colon interior, all colon points thus found also lie in the interior of the colon. Each end point found in this way is subsequently marked by the method with the length of the route segment covered.

In further iterations, the search is now expanded from all the end points found by new route segments that once again run completely along the air voxels. These end points are now marked with the sum of the length of the new route segment and the distance value noted at the previous end point. If in so doing the method repeatedly hits an identical end point, the end point is marked with the minimum of these sums at the respective end point. Such an end point is therefore not considered further during further iterations. The expansion of the end points is repeated until an end point in the ambient air is found. The calculated route sum of this end point is the approximated rectum distance.

The search method can be optimized with the aid of a list of the end points that is ordered according to accumulated distance. In this case, it is respectively only the end point that exhibits the smallest accumulated distance to date which is expanded by reading this end point from the top of the list. The search thereby expands uniformly in all spatial directions.

The end points can additionally be ordered with the aid of a penalty function that incorporates the distance of the respective end point from the colon wall or from the skeleton of the colon or from a path previously covered by the endoscope. Use is made here of a heuristic weighting of accumulated distance and distance to the walls/middle line of the colon. The search thereby preferably expands along the middle line of the colon and finds the rectum thus after a few iterations.

The distance value is approximated owing to the search along the directions of the principal axes, since the endoscope follows a rectilinear course when being advanced, whereas the distance is measured along a stepped course whose size is governed by the length of the rectilinear route segments. The approximation quality can be improved when the search is also expanded in diagonal directions in addition to the directions of the principal axes.

After an end point has been found in the ambient air, a similar effect can be achieved by backtracking on the path leading from the starting point to this end point and smoothing it, for example by leaving out individual end points. It must be checked in this case whether the newly produced route segments run along air voxels, that is to say run inside the colon.

The abovedescribed embodiment of a method shows only one of the possible variants of image processing. Other known processing methods for automatic path calculation can likewise be used without departing from the scope of the invention.

Since the colon can also become partially blocked during image acquisition, situations can arise in which the above-described Dijkstra method does not find the rectum. However, this problem can be overcome according to at least one embodiment of the invention by using at least two image data records of the patient, recorded in different positions.

For example, one data record of the patient can be acquired in prone position, and one in supine position. In one refinement of an embodiment of the method, the course of the colon of the two data records can then firstly be brought into spatial correspondence with one another, for example via a registration method described further below. The partial blockages can now be bridged by combining the two data records in a suitable way when identifying air voxels, for example by way of an OR operation or by forming an envelope.

Since the anatomy of the colon exhibits anatomical features—for example appendix (caecum), vermiform appendix, right or left curve (right colic flexure or left colic flexure), ileum (sinus)—that vary only slightly from patient to patient in the rectum distance, the rectum distance can be determined with the aid of these additional features. If the reverse distance measurement encounters one of these features, the distance measurement can either terminate and add the mean statistical rectum distance of the feature to the distance determined up to this point, or the distance measurement can continue and output a mean value determined from both distances, or if appropriate from distances determined at a number of features.

A particular design of the method according to an embodiment of the invention is illustrated in FIGS. 2 to 5. These FIGS. 2 to 5 show a simplified representation of a colon $C_1$ and $C_2$, respectively in FIGS. 2 and 3, recorded in conjunction with different positions of the patient. By way of example there is shown in each representation of the colon in FIGS. 2 and 3 a blockage $V_1$ and $V_2$, respectively, at which an automatic path calculation would lead to a stop, since here there is no longer any air-filled space that would enable a path calculation.

Figure 4:
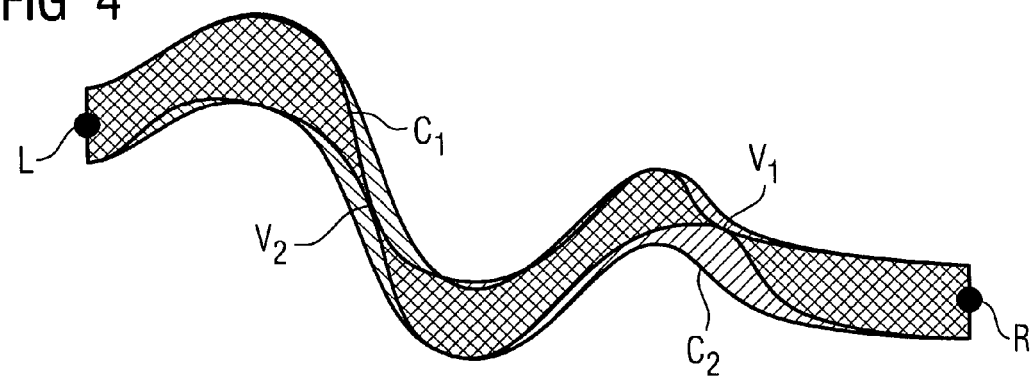

According to an embodiment of the invention, in FIG. 4 the two volumes of the colons $C_1$ and $C_2$ are superposed such that both the positions of the lesion L and the rectum R are identical, and a total path of the two colons $C_1$ and $C_3$ is subsequently determined via the sum of the paths by means of an OR operation or by performing an envelope.

Figure 5:
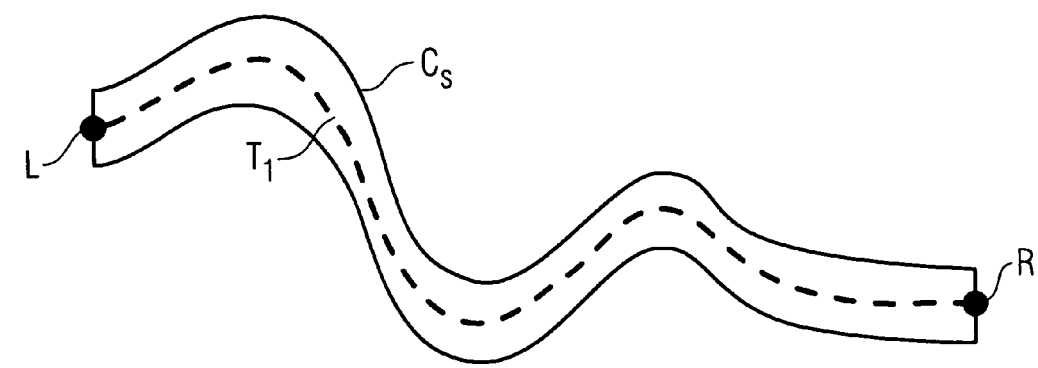

The sum of the colon Cs thus determined is illustrated in FIG. 5. Fundamentally, it corresponds to an envelope of the two colon paths $C_1$ and $C_2$ from FIG. 4. There are no more blockages to be seen in this additive representation of FIG. 5, and so the path T between the lesion L and the rectum R can be calculated by automatic path calculation without premature stoppage, the rectum distance of the lesion thereby being determined.

Another variant of the path determination is illustrated in FIGS. 6 to 9.

Figure 6:
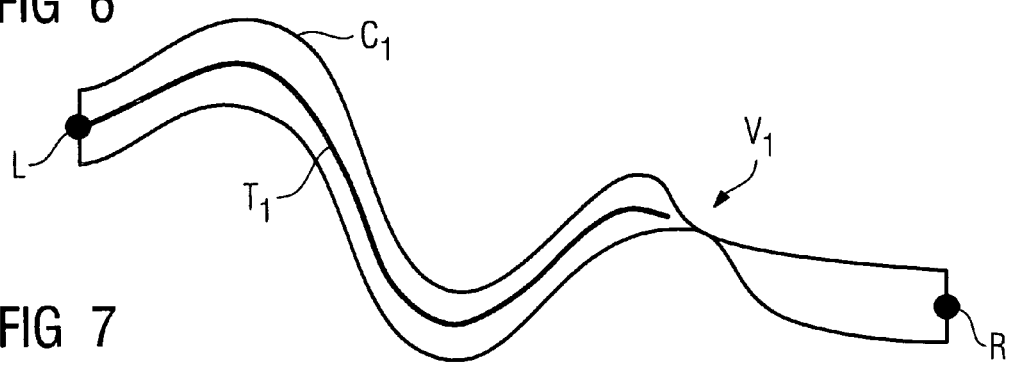

FIG. 6 shows a first picture of the colon $C_1$ with a blockage $V_1$ relatively near the rectum R. Starting at the lesion L, the path $T_1$ thus calculated reaches as far as the blockage $V_1$.

Figure 7:
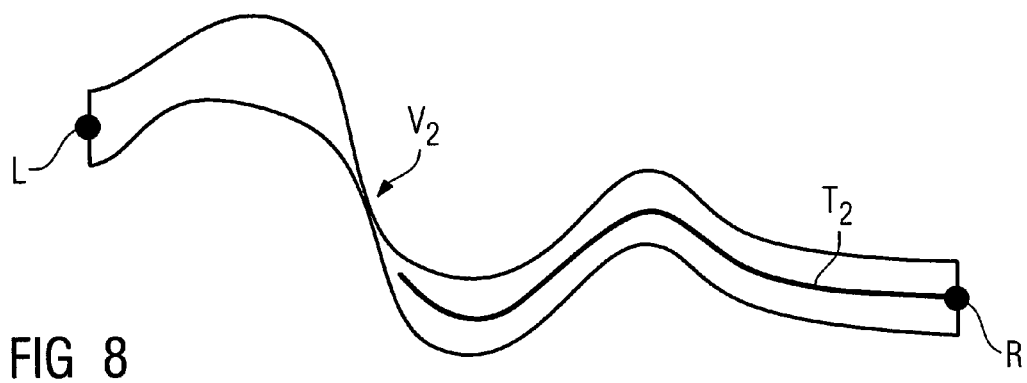

At the same time, FIG. 7 illustrates a path $T_2$ that, starting from the rectum R, reaches up to the blockage site $V_2$ shown there, which here is present relatively near the lesion L.

Figure 8:
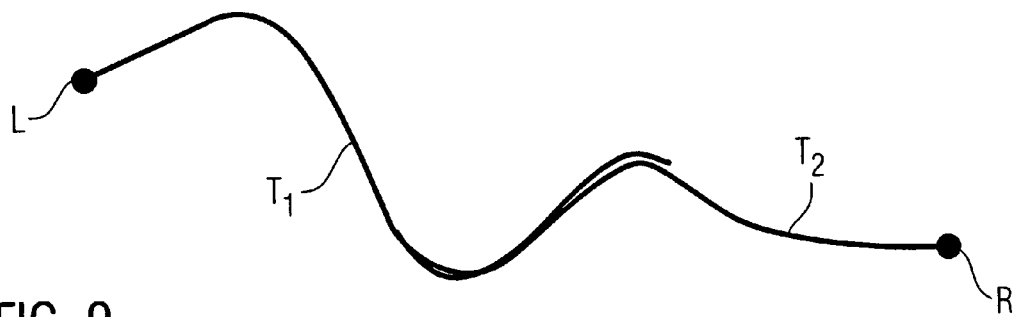
Figure 9:
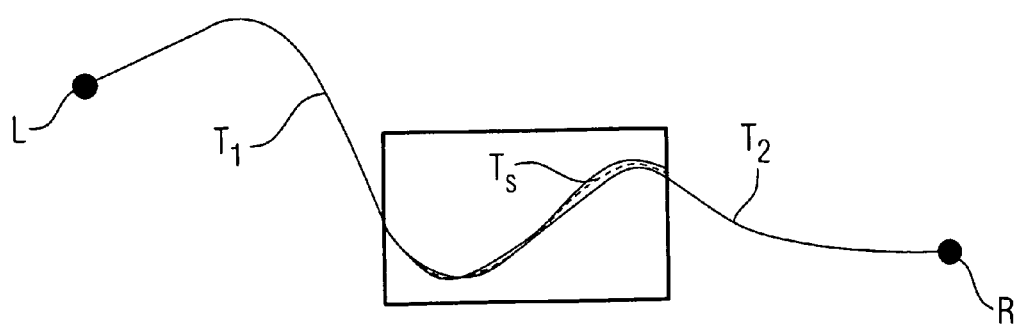

FIG. 8 then shows the two paths $T_1$ and $T_2$—without displaying the colon—and FIG. 9 illustrates the formation of the sum of these two paths $T_1$ and $T_2$ to form a common path $T_S$. Thus, the total path between the lesion L and the rectum R is thereby determined in FIG. 9 by way of the sum of the paths and an appropriate formation of the mean in the region of the box.

It is pointed out in this regard that a very similar calculation is also possible by virtue of the fact that, for example, the paths are respectively calculated in FIGS. 6 and 7 starting from the lesion and from the rectum such that gaps exist in the path calculation only at the two blockage sites $V_1$ and $V_2$, it being possible to determine the total path subsequently by forming the sum—as has been illustrated in FIGS. 8 and 9.

A further embodiment of the inventive automatic distance calculation in the colon is illustrated in FIGS. 10 and 11. FIG. 10 shows an example colon $C_1$, recorded in a first position of a patient, this colon additionally having a salient point P that is determined by the vermiform appendix A present there. Starting again from the lesion L, the path calculation of the path $T_1$ in FIG. 10 leads via the salient point P up to the blockage $V_1$, where the path stops. Illustrated correspondingly in FIG. 11 is the same colon $C_2$ with a different position, the blockage in this case being present at a site between the lesion L and the salient point P. Starting from the rectum R, the path $T_2$ was correspondingly calculated via the salient point P up to the blockage site $V_2$. If the distance between the lesion L and the salient point P is extracted from FIG. 10, and the distance from the salient point P up to the rectum R is extracted from FIG. 11, and the two subpath routes are added up, the sum of these subpath routes corresponds to the entire distance between the lesion L and the rectum R.

Another inventive possibility of path calculation is finally illustrated in FIG. 12. Here, a colon $C_1$ is represented in a single position, a blockage site $V_1$ being present in the vicinity of the rectum. According to an embodiment of the invention, the path $T_1$ between the lesion L and a salient point P is calculated on the basis of a 3D picture. The rectum distance of the salient point P is reliably well known from statistical surveys, and so the actual distance of the lesion L from the rectum can be determined by adding up the calculated route $T_1$ and the statistically known rectum distance of the salient point P.

An improved variant of this design can be provided, for example, by additionally measuring further distances through using other colon pictures with different positions of the patient such that an improved evaluation is thereby possible by forming the mean of the rectum distances thus determined from the lesion. In addition, such a distance calculation between two salient points in the colon can be used, for example, to calculate the deviation of the patient's own values from statistical mean values such that these patient-specific differences can also be introduced into the calculation.

Thus, there is the possibility of measuring the actual distance between two salient points, and also of transferring the change in relation to its statistical value onto other statistical values so as to enable an improved accuracy of the determination of distance from the combination of actually measured values and statistically available values.

In particular variants of embodiments of the invention, use is made of a so-called registration method by which two n-dimensional, medical data records of the same body region are brought into spatial or temporal correspondence by means of global rigid, affine, projective or curvilinear transformations or, in addition, by means of local transformation similar to a morphing method.

The input data records can have been produced in this case both by a single patient and by different patients in the same or different positions (for example supine/prone positions). Moreover, it is possible in principle for image data of the same modality such as CT-CT, MR-MR, etc., or else of two different modalities such as CT-PET, MR-SPECT, etc., to be registered with one another.

FIG. 13 is a schematic of the registration of two geometric figures, i.e. square and circle. Here, in the course of the registration an iterative optimization method is used to transform a data record in small steps until a position of maximum correspondence to the second reference data record is found. In general, such a method therefore operates in two steps in each iteration, as illustrated in the method scheme in FIG. 14, specifically the transformation by a suitable $\delta$ and an evaluation of the correspondence previously found.

In detail, the method steps are:
1: beginning of the registration with two n-dimensional image data records of initially different alignment;
2: transformation by $\delta$;
3: evaluation of the correspondence;
4: optimum achieved?;
5: path for "yes";
6: path for "no"; and
7: result with two n-dimensional image data records of identical alignment.

The transformation can effect both a global change in the overall data cube (rotation, translation, scaling, shearing, etc.), and transform individual partial cubes locally in accordance with different rules. After each transformation step, the quality of the correspondence found is determined by way of a suitable evaluation method, for example sum of the difference of the position of manually set, correlating markers; sum of the voxel intensity differences; correlation of the intensities; maximum mutual information, and the direction and size of the next step are determined if appropriate. The method terminates when it is no longer possible to find any improving step direction, that is to say when a locally optimum transformation of the initial data record into the reference data record is found.

By analogy with the abovedescribed registration method, it is also possible to produce on the basis of a multiplicity of n patient data records an anatomical atlas or reference image data record that reflects an average patient anatomy and, in addition, a measure of local deviations.

To this end, all n data records can firstly be registered by rigid transformations in order to eliminate the transformation given by the picture and different patient positions. Subsequently, an initial data record is transformed elastically using n patient data records such that it has a maximum sum of correspondence or minimum quadratic deviation with these n data records.

If such a method is carried out to produce a colon atlas, the method according to an embodiment of the invention can be used to determine an average rectum distance for each point $P_x$ in the colon $C_a$ and stored with the atlas. Such an atlas is illustrated by way of example in FIG. 15.

The rectum distance stored in the atlas can be used in order to determine the rectum distance of a point in the colon of the patient being examined. To this end, one (or more) acquired patient data record is registered with the anatomical atlas. Subsequently, the point marked in the patient data record can be identified in the atlas, and the rectum distance stored for this point can be output in a suitable combination with further measurements.

FIG. 16 shows schematically here the result of the registration of a colon picture $C_1$ of a current patient colon with the aid of an atlas image $C_a$.

It remains to be pointed out in addition that the colon pictures registered in relation to reference images can also be produced as a function of patient-specific data such as age, size, sex, etc., atlas images with similar or identical patient-typical features respectively being used in the design of the method in accordance with an embodiment of the invention.

It goes without saying that the abovementioned features of embodiments of the invention can be used not only in the respectively specified combination, but also in other rational combinations, in particular in combinations other than specified in the patent claims that are referred back, or on their own, without departing from the scope of the invention.

Thus, overall, at least one embodiment of the invention proposes the use of a method known per se for the purpose of computer-aided determination of the rectum distance between a selected site and the rectum, the path between the rectum and selected site being determined by common perusal from at least two 3D image data records, either recorded with different positions of the patient, or with at least one 3D image data record of the patient and at least one statistically relevant reference 3D image data record. The common perusal can reside in this case both in an initial processing of the at least two image data records to form a common image data record and subsequent application of a known automatic path determination, or else in the common perusal of the previously calculated paths on the basis of a number of unprocessed image data records, errors in the path calculation being compensated here. Of course, the invention also incorporates a combination of these two last mentioned basic types of the method according to at least one embodiment of the invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for automatically determining a rectum distance in a colon of a patient, comprising:
   recording at least two 3D image data records of the colon, each recorded with the patient being differently positioned; and
   determining a path in the colon between a selected site and the rectum by processing the 3D image data records, the path between the rectum and selected site including at least one blockage in the colon and being determined from a common perusal of the at least two 3D image data records, the processing excluding registration between the at least two 3D image data records; wherein
   for each of the at least two 3D image data records,
      an automatic path calculation is carried out in relation to a plurality of salient points in the colon,
      subpath lengths between the plurality of salient points are determined, and
      a total path length between the selected site and the rectum is determined from all determined subpath lengths.

2. The method as claimed in claim 1, wherein the total path is calculated from a sum of at least one of mean values, meridian values, and arithmetic means of the determined subpath lengths.

3. The method as claimed in claim 2, wherein the automatic path calculation begins both at the rectum and at the selected site in the colon.

4. The method as claimed in claim 2, wherein the automatic path calculation begins exclusively at the selected site in the colon.

5. The method as claimed in claim 2, wherein a Dijkstra method is used for the automatic path calculation.

6. The method as claimed in claim 1, wherein the automatic path calculation begins both at the rectum and at the selected site in the colon.

7. The method as claimed in claim 1, wherein the automatic path calculation begins exclusively at the selected site in the colon.

8. The method as claimed in claim 1, wherein a Dijkstra method is used for the automatic path calculation.

9. A method for automatically determining a rectum distance in a colon of a patient, comprising:
   recording at least two 3D image data records of the colon, each recorded with the patient being differently positioned; and
   determining a path in the colon between a selected site and the rectum by processing the 3D image data records, the path between the rectum and selected site including at least one blockage in the colon and being determined from a common perusal of the at least two 3D image data records, the processing excluding registration between the at least two 3D image data records; wherein
   for at least one of the at least two 3D image data records,
      an automatic path calculation is carried out in the colon in relation to at least one salient point whose mean statistical distance from the rectum is at least one of,
         constant and independent of the patient, and
         a function of other patient parameters, and
      a path length to the rectum is determined from a sum of the automatically calculated path and a distance, which does not depend on the patient.

10. The method as claimed in claim 9, wherein the automatic path calculation begins both at the rectum and at the selected site in the colon.

11. The method as claimed in claim 9, wherein the automatic path calculation begins exclusively at the selected site in the colon.

12. The method as claimed in claim 9, wherein a Dijkstra method is used for the automatic path calculation.

13. A method for automatically determining a rectum distance in a colon of a patient, comprising:
   recording at least two 3D image data records of the colon, each recorded with the patient being differently positioned; and
   determining a path in the colon between a selected site and the rectum by processing the 3D image data records, the path between the rectum and selected site including at least one blockage in the colon and being determined from a common perusal of the at least two 3D image data records, the processing excluding registration between the at least two 3D image data records; wherein
      a typical colon volume data record is produced by registering a multiplicity of colon pictures of various persons, and is registered with at least one picture of a currently examined patient, and an automatic path calculation relating to the rectum is determined from the produced typical colon volume data record.

14. The method as claimed in claim 13, wherein the automatic path calculation begins both at the rectum and at the selected site in the colon.

15. A method for automatically determining a rectum distance in a colon of a patient, comprising:
   recording at least two 3D image data records of the colon, each recorded with the patient being differently positioned; and
   determining a path in the colon between a selected site and the rectum by processing the 3D image data records, the path between the rectum and selected site including at least one blockage in the colon and being determined from a common perusal of the at least two 3D image data records, the processing excluding registration between the at least two 3D image data records; wherein
   a typical colon volume data record is produced by registering a multiplicity of colon pictures of various persons, and is registered at least partially with at least one picture of the currently examined patient,
   an automatic path calculation relating to at least one salient point is determined from the produced typical colon volume data record, and
   from a sum of a distance of the automatic path calculation and a known distance of the at least one salient point, the distance to the rectum is determined from the typical colon volume data record known by registration of the multiplicity of colon pictures of various persons.

16. The method as claimed in claim 13, wherein the automatic path calculation begins exclusively at the selected site in the colon.

17. The method as claimed in claim 13, wherein a Dijkstra method is used for the automatic path calculation.

18. The method as claimed in claim 15, wherein the automatic path calculation begins both at the rectum and at the selected site in the colon.

19. The method as claimed in claim 18, wherein the automatic path calculation begins exclusively at the selected site in the colon.

20. The method as claimed in claim 18, wherein a Dijkstra method is used for the automatic path calculation.

* * * * *